United States Patent [19]

Medvick

[11] 4,114,853

[45] Sep. 19, 1978

[54] QUICK CONNECT COUPLING

[75] Inventor: Richard J. Medvick, Bedford, Ohio

[73] Assignee: Swagelok Company, Hudson, Ohio

[21] Appl. No.: 730,941

[22] Filed: Oct. 8, 1976

[51] Int. Cl.² .................. F16L 29/00; F16L 37/28
[52] U.S. Cl. .................................. 251/149.6; 285/316
[58] Field of Search ............... 251/149.6; 136/614.03, 136/614.04; 285/316

[56] References Cited

U.S. PATENT DOCUMENTS

| Re. 23,120 | 6/1949 | Earle et al. ................... 285/316 X |
| 3,170,667 | 2/1965 | Szohatzky ....................... 251/149.6 |
| 3,221,178 | 10/1965 | Kiszko ............................ 137/614.04 |
| 3,474,827 | 10/1969 | Torres ........................... 251/149.6 X |

Primary Examiner—William R. Cline
Attorney, Agent, or Firm—Fay & Sharpe

[57] ABSTRACT

A quick connect coupling includes interfitting male and female members carrying cooperable releasable coupling parts for releasably coupling the members. The coupling parts include a cooperating projection and recess dimensioned for closely fitting together when the members are interfitted in coupled relationship. The recess on one of the coupling parts is defined between relatively movable inner and outer sleeves. Each coupling part is ineffective to couple with any other coupling part lacking a properly dimensioned and located projection or recess.

19 Claims, 8 Drawing Figures

QUICK CONNECT COUPLING

BACKGROUND OF THE INVENTION

This application pertains to the art of couplings and, more particularly, to couplings of the so-called quick connect type. The invention is especially related to coupling of fluid conduits and will be described with particular reference thereto. However, it will be appreciated that the invention has broader aspects and may be used for coupling other conduits and cables or the like.

Quick connect couplings are commonly used in panel board installations where a plurality of different fluid lines are to be connected with several different devices. For example, pressure lines may run from a particular machine to a panel board for connection by quick connect couplings to a series of measuring devices. Hospitals using various gases including oxygen and anesthetic also use quick connect couplings for feeding the gas to a particular type of equipment.

In systems of the type described, care must be exercised to be sure that the proper source of fluid is connected with the proper piece of equipment. Otherwise, damage to the equipment or serious injury to a person may result. In order to alleviate this problem, various color codes, labels and non-interchangeable quick connect couplings have been used. One known type of keyed or coded quick connect system is disclosed in U.S. Pat. No. 3,170,667 issued Feb. 23, 1965, to Szohatzky. In the Szohatzky arrangement, a male member carries a male coupling part having an elongated axially extending cylindrical projection. The female member carries a coupling part having an axially extending recess for receiving the projection when the male and female members are interfitted. A system of couplings is coded by having projections and recesses of varying diameters or radial thicknesses so that each coupling part of a mating pair will not mate with other coupling parts because the projections and recesses will not fit together.

The Szohatzky coupling is arranged so that a coded male or female coupling part will respectively couple with a standard non-coded female or male coupling part. This type of arrangement has been found to be undesirable because coupling of standard coupling parts with coded coupling parts presents potential health hazards and may damage delicate equipment if improper connections are made.

In the Szohatzky coupling, the female coupling part having the recess is essentially a one-piece sleeve. This means that the terminal ends of the sleeve on radially outer and inner sides of the recess openings are always located in the same relative axial position. Furthermore, the axially extending projection on the male coupling part is located intermediate the inner and outer surfaces of that part.

In arranging coded coupling systems, it is desirable to use standard interfitting male and female members. When placing the coded male and female coupling parts of the type disclosed in the Szohatzky patent on standard male and female members, careful tolerance requirements must be maintained in order to achieve a coded coupling system wherein the coded coupling parts will not couple with non-mating coded coupling parts or with non-coded standard coupling parts.

SUMMARY OF THE INVENTION

A quick connect coupling includes interfitting male and female members having cooperating releasable coupling means for releasably coupling the members. The coupling means includes cooperating projection and recess means dimensioned for closely fitting together when the members are coupled. The recess means is defined between inner and outer sleeves forming part of the coupling on one of the members, and the sleeves are axially movable relative to one another.

In a preferred arrangement, the inner and outer sleeves are on the female member, and the inner sleeve is movable relative to the outer sleeve axially outwardly to an unlocking position and axially inwardly to a locking position. Yieldable biasing means normally biases the inner sleeve to its unlocking position.

The male coupling member includes a male sleeve having a cylindrical extension defining the projection means which fits closely into the recess. The inner and outer sleeves have radially spaced outer terminal ends between which an entrance opening to the recess means is defined. The outer terminal end of the inner sleeve is spaced a substantial distance axially inward of the outer terminal end of the outer sleeve at least when the members are coupled with the extension received in the recess means.

The outer sleeve is preferably movable axially relative to the female member and to the inner sleeve. Axial movement of the outer sleeve provides for movement of the inner sleeve to its unlocking position for uncoupling the male and female members.

The inner sleeve may cooperate with locking detents movable radially inward to a coupling position and outwardly to a releasing position. The detents cooperate with a groove in the male member when the male and female members are interfitted. The inner sleeve is yieldably biased to its unlocking position by a first force, and the male sleeve is biased outwardly with a second force greater than the first force. When the male and female members are interfitted with a projection properly received in a cooperating recess, a shoulder on the male coupling part engages the outer terminal end of the inner sleeve so that the second force overcomes the first force and moves the inner sleeve to its locking position for holding the detents in their coupling position.

At least one of the male and female members includes normally closed fluid control means which is opened when the members are interfitted over a predetermined axial length. Each male and female member is respectively interfittable over said predetermined length and is coupleable only with female and male members having coupling means with a projection or recess dimensioned for closely fitting together with the recess or projection on the cooperating releasable coupling means. This arrangement positively prevents improper coupling of one conduit with another.

The improved coupling is used in a system of couplings for interfitting male and female members, at least one of which includes normally closed fluid control means which is opened when the members are interfitted over a predetermined axial length. The members have cooperating releasable coupling means for releasably coupling the members. The coupling means includes a plurality of different mating pairs of coded male and female coupling parts respectively having closely interfitting projections and recesses so that the projection and recess on a mating pair of male and female coupling parts will not interfit with a recess or projection respectively on other non-mating coded coupling parts. The coded male and female coupling parts prevent interfitting of male and female members carrying same over the predetermined axial length to open the fluid control means unless the coded coupling parts thereon are a mating pair. The system of couplings includes a plurality of mating pairs of standard non-coded male and female coupling parts all cooperable with one another and lacking any interfitting projections and recesses. The coded male and female coupling parts respectively are incapable of interacting with the standard non-coded female and male coupling parts to positively releasably couple male and female members interfitted over the predetermined axial length.

It is a principal object of the present invention to provide a non-interchangeable quick connect coupling.

It is also an object of the present invention to provide a quick connect coupling which is coded to positively prevent coupling with non-mating coded coupling parts or with standard non-coded coupling parts.

It is an additional object of the invention to provide an improved coded coupling which can easily be added to standard interfitting male and female members.

It is an additional object of the invention to provide a quick connect coupling wherein the female coupling part includes relatively axially movable inner and outer sleeves between which an axially extending recess is defined for receiving a projection on a cooperating male coupling part.

It is also an object of the invention to provide an improved system of couplings having coded mating pairs of coupling parts which will not couple with different mating pairs of coupling parts or with standard non-coded coupling parts.

DESCRIPTION OF PREFERRED EMBODIMENTS

Figure 1:
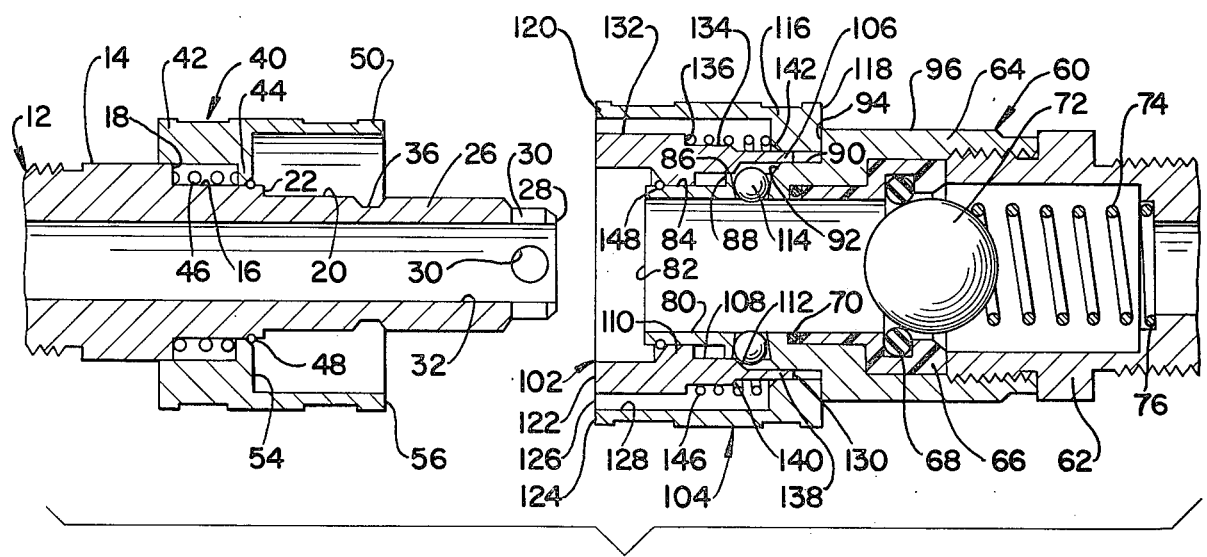
FIG. 1 is a cross-sectional elevational view of male and female members carrying coupling parts and positioned for being interfitted.

With reference to the drawings, FIG. 1 shows a hollow male member 12 in the form of a fitting adapted for attachment to a hose or other fluid conduit. The male member 12 has an external large cylindrical portion 14 intersecting a smaller intermediate cylindrical portion 16 at a radially extending shoulder 18. The intermediate cylindrical portion 16 intersects a small cylindrical portion 20 at a radial shoulder 22. The small cylindrical portion 20 is on an elongated stem 26 having a reduced diameter outer terminal end portion which terminates at stem end 28. A plurality of circumferentially-spaced radial holes 30 through the terminal end portion of the stem 26 slightly inwardly from stem end 28 provide flow from internal bore 32 to the exterior of the stem 26. An external circumferential groove 36 is formed in the stem 26 a substantial distance inwardly from the stem end 28.

A male coupling part 40 in the form of a generally cylindrical male sleeve is carried by the male member 12. The coupling part 40 has an inner end portion 42 slidably supported on the large cylindrical portion 14 of the male member 12. An inwardly extending cylindrical flange 44 is slidably supported on the intermediate cylindrical portion 16. A yieldable biasing means in the form of a coil spring 46 has its ends bearing against the shoulder 18 and the flange 44 to normally bias the male sleeve 40 to the right in FIG. 1 so that the flange 44 abuts a stop defined by a metal snap ring 48 positioned in a suitable groove in the surface of the intermediate cylindrical portion 16 adjacent the shoulder 22. An elongated cylindrical extension 50 defines an axially extending projection which extends outwardly from the male sleeve or coupling part 40. The projection 50 has an outer surface which is substantially flush with the outer surface of the male sleeve or coupling part 40. The slight steps in the outer surface of the male sleeve 40 are simply for knurling to enable a firm grip thereon. The inner surface of the projection 50 intersects the inner end portion 42 of the male sleeve 40 at a generally radially extending shoulder 54 which preferably does not extend axially outwardly beyond the abutment stop defined by the snap ring 48. This provides an extremely long length for all of the projections 50 in a coupling system between the projection outer end 56 and the shoulder 54.

A hollow female member 60 in the form of a fitting for attachment to hose or conduits is cooperable with the male member 12. The female member 60 is conventional and may include one part 62 secured to another part 64 and also securing a carrier 66 therein for an O-ring 68. The carrier 66 also traps an O-ring 70 within the part 64. A suitable fluid control means shown in the form of a ball 72 is normally biased to a closed position in engagement with the O-ring 68 by a spring 74 bearing against the ball 72 and a shoulder 76 in the part 62.

The female member 60 has a cylindrical bore 80 of a diameter for closely receiving the stem 26 on the male member 12. The distance between the ball 72 and terminal open end 82 of the female member 60 is less than the length of the male stem 26 from the shoulder 22 to the stem end 28 so that interfitting of the male and female members by positioning the stem 26 within the bore 80 causes the stem end 28 to engage the ball 72 and move same to the right in FIG. 1 to an open position out of engagement with the O-ring 68 for flow of fluid therepast. Although the arrangement shown and described includes a fluid control means in only one of the interfitting members, it will be recognized that such a fluid control means can be located in either or both of the male and female members 12 and 60. Where a fluid control means is located in both members, they are opened substantially simultaneously when the coupling is effected, and are closed substantially simultaneously when the parts are uncoupled.

The female member 60 has a small cylindrical portion 84 extending axially inwardly from the terminal open end 82 thereof and intersecting a larger intermediate cylindrical portion 86 at a shoulder 88. The intermediate cylindrical portion 86 intersects a large cylindrical portion 90 at a shoulder 92. Large cylindrical portion 90 extends outwardly at a shoulder 94 to outer surface 96 of the female member 60.

The female member 60 carries a female coupling part in the form of inner and outer sleeves 102 and 104 respectively. For purposes of description, the sleeves 102 and 104 may also be called sleeve parts as in certain forms they could be connected together or form part of a common sleeve. The inner sleeve 102 has an inner end portion 106 slidably supported on large cylindrical portion 90. An intermediate portion 108 of the inner sleeve 102 is slidably supported on the intermediate cylindrical portion 86. An inwardly extending cylindrical projection 110 provides another inner sleeve surface slidably supported on small cylindrical portion 84. The inner end portion 106 of the inner sleeve 102 intersects the intermediate portion 108 thereof at an inwardly and outwardly extending cam shoulder 112.

A plurality of locking detents in the form of balls 114 are positioned in suitable tapered bores through the female member 60 at the intermediate cylindrical portion 86 thereof for movement between radially inward locking or coupling positions and radially outward releasing positions.

The outer sleeves 104 have a cylindrical inner or base portion 116 slidably supported on the inner end portion 106 of the inner sleeve 102. The inner or base end 118 of the outer sleeve 104 normally abuts the shoulder 94 on the female member 60. An elongated cylindrical extension 120 extends outwardly from the base 116 of the outer sleeve 104.

The terminal ends 122 and 124 of the inner and outer sleeves 102 and 104 respectively are radially spaced-apart to define an outwardly facing axial opening 126 to an elongated cylindrical axial recess 128 formed by having the sleeves 102 and 104 radially spaced over a substantial portion of their length inwardly from their outer terminal ends. The inner surface of the extension 120 on the outer sleeve 104 is substantially cylindrical and of uniform diameter. The outer surface of the inner sleeve 102 is also cylindrical but is stepped inwardly along its length from its outer terminal end 122 toward its inner terminal end 130. The inner sleeve 102 has a large external cylindrical surface 132 extending inwardly from the outer terminal end 122 thereof and intersecting an intermediate cylindrical portion 134 at a radial shoulder 136. The intermediate cylindrical portion 134 intersects a small cylindrical portion 138 adjacent the inner terminal end 130 at a sloping shoulder 140 axially aligned with the corresponding sloping shoulder 142 on the base 116 of the outer sleeve 104. The intermediate cylindrical portion 134 defines a spring cavity inward of the recess 128 and receives a yieldable biasing means in the form of a coil spring 146 having its end bearing against the shoulder 136 and the base portion 116 of the outer sleeve 104. The spring 146 biases the inner and outer sleeves 102 and 104 apart to the positions shown in FIG. 1 with the base end 118 of the outer sleeve 104 bearing against the shoulder 94 on the female member 64, and with the flange 110 on the inner sleeve 102 bearing against an abutment stop defined by a metal snap ring 148 received in a suitable circumferential groove adjacent the terminal open end 82 of the female member 60.

In the arrangement shown and described, at least the inner sleeve 102 is axially movable relative to the female member 60 and the outer sleeve 104. In the preferred arrangement, the outer sleeve 104 is also axially movable relative to the female member 60 and the inner sleeve 102. The spring 146 normally biases the inner sleeve outwardly to an unlocking position wherein the inner end portion 106 is aligned with the balls 114 so that the balls 114 are free to move to their outer released positions. Axially inward movement of the inner sleeve 102 causes cam surface 112 to move the balls 114 inwardly to their locking or coupling positions where they are held by the intermediate portion 108 of the inner sleeve 102. The terminal ends 122 and 124 of the inner and outer sleeves 102 and 104 are axially aligned with one another when the parts are not coupled as shown in FIG. 1. The axial length of the recess 128 from the terminal ends of the sleeves to the bottom of the recess is substantially longer than the length of the male projection 50 when the parts are not coupled. However, after the parts are coupled, the length of the recess is substantially the same as the length of the projection 50. The terminal outer end 122 of the inner sleeve is located a substantial distance axially outward from the terminal open end 82 in the unlocking position of the inner sleeve as shown in FIG. 1. After coupling, the terminal end 122 is located a substantial distance inwardly from the open end 82. This relationship, along with having the shoulder 54 located closely adjacent the stop 48, is very important to the invention for preventing coupling of non-coded or improperly coded parts.

Figure 2:
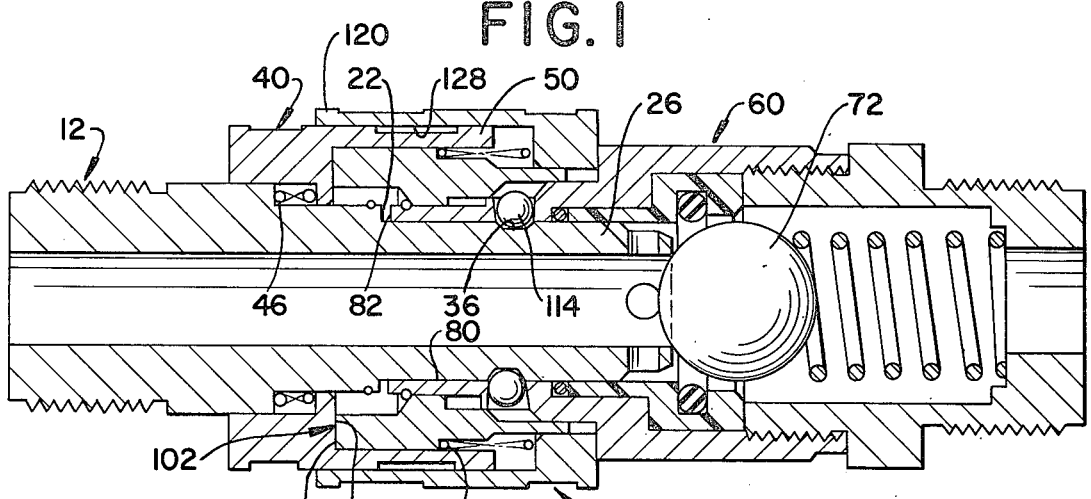
FIG. 2 is a cross-sectional elevational view of the members of FIG. 1 in an intermediate coupled position.

FIG. 2 shows an intermediate position of the parts just before they are coupled or as they are about to be uncoupled. An external pushing force has been applied to the male member 12 for moving same to the right in FIG. 2 and compressing the spring 46. The recess 128 is located and dimensioned for closely receiving the projection 50 so that the stem 26 moves into the bore 80 to open the fluid control means 72. As the stem 26 moves into the bore 80, the stem 26 biases the detent balls 114 in a radially outward position. The balls 114 in this outward position interfere with cam surface 112 in such a way to prevent axial movement to the right of inner sleeve 102. Due to engagement of outer terminal end 122 of the inner sleeve 102 with shoulder 54 of male sleeve 40, spring 46 is compressed by the external pushing force being applied to male member 12. When male member 12 has been moved to the right sufficiently to locate groove 36 radially inward of the detent balls 114, the component parts will generally be as shown in FIG. 2. Locating groove 36 radially iwnard of balls 114 frees the balls to move inward into the groove. Through abutting members this freedom of balls 114 frees the coil spring 46 which exerts a substantially greater force than the spring 146. This will cause the male sleeve 40 to move to the right in FIGS. 2 and 3 and, due to the engagement of the shoulder 54 with the outer terminal end 122 of the inner sleeve 102, the inner sleeve will be axially moved inwardly to its locking position shown in FIG. 3 so that the balls 114 are positioned in the groove 36. In the coupled position of the parts shown in FIG. 3, the outer terminal end 122 of the inner sleeve 102 is axially spaced a substantial distance inwardly from the outer terminal end 124 of the outer sleeve 104. This reduces the total length of the recess 128 and also allows the projection 120 on the outer sleeve 104 to overlie the male sleeve 40 over a greater axial length. The terminal end 124 of the outer sleeve 104 actually moves well past the internal shoulder 54 on the male sleeve 40.

Figure 3:
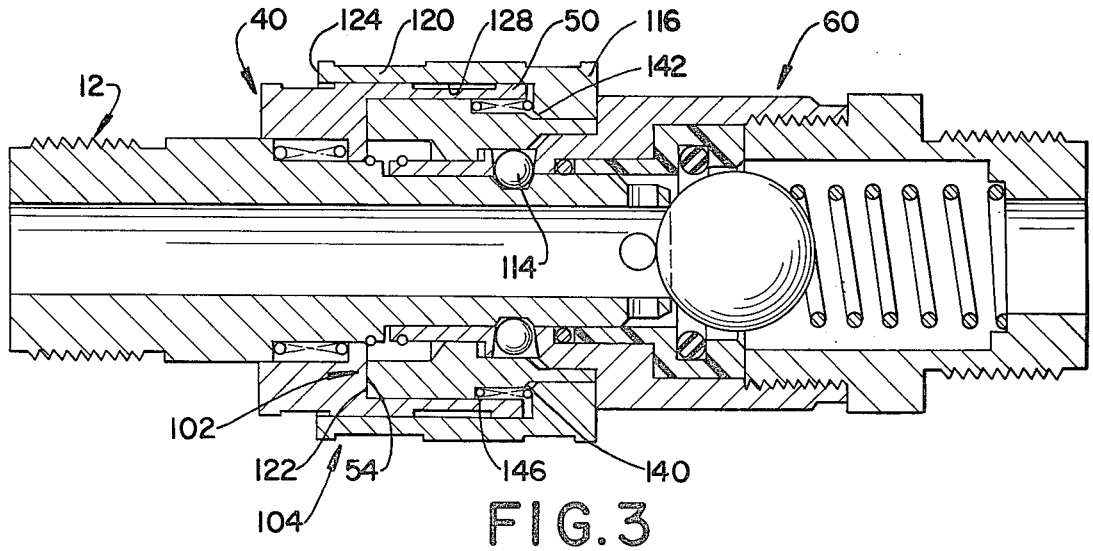
FIG. 3 is a cross-sectional elevational view of the members in coupled relationship.

In order to uncouple the members from the coupled relationship of FIG. 3, it is possible to apply pulling force to the male sleeve 40 so that the parts will return to the position of FIG. 2 for uncoupling. However, it is also possible to apply an axial pulling force on the outer sleeve 104 so that the surface 142 on the base portion 116 will strike against the shoulder 140 on the inner sleeve 102 as the spring 146 is compressed to positively move the inner sleeve outwardly from its locking position to free the balls 114 for outward movement to their releasing positions. The distance between the shoulder 140 and 142 is such that they will engage one another before the spring 146 is bottomed out and this aids in minimizing high stresses on the spring. This advantageous arrangement also makes uncoupling very easy because either the male or female sleeve can be pulled for uncoupling the members. This is particularly advantageous where the projection 120 on the outer female sleeve 104 overlies the male sleeve 40 to such an extent that it is difficult to obtain a firm grip thereon for uncoupling the parts.

Figure 5:
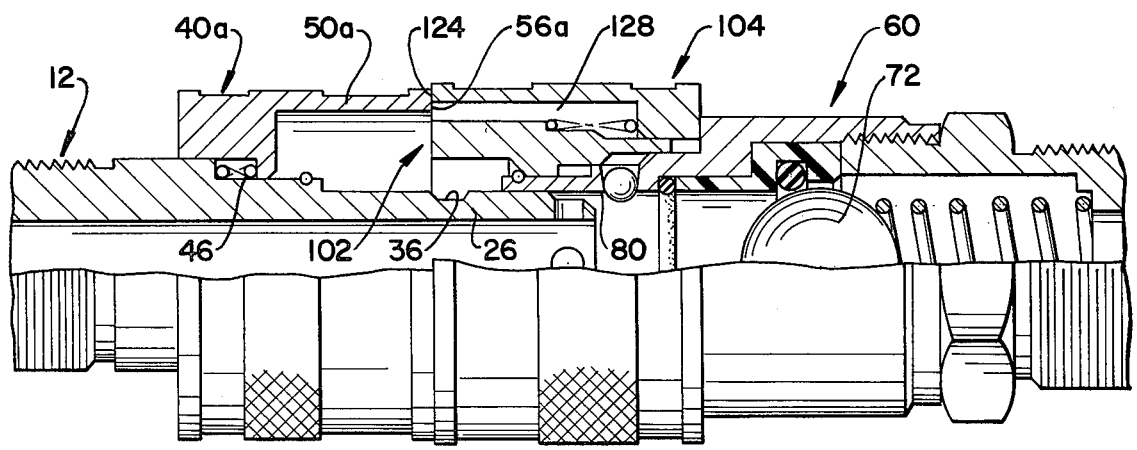
FIG. 5 is a partial cross-sectional elevational view showing members having coupling parts which are non-mating.

In the arrangement shown and described, it has been found that existing standard male and female members can be converted to have coded coupling parts simply by attaching the described coupling sleeves thereto. In a system of couplings, the mating pair of coded male and female coupling parts have a projection as at 50 and a recess as at 128 which are dimensioned and positioned to closely fit together when the members are coupled. A plurality of different pairs of mating coded coupling parts have their projections and recesses of different diameters so that a recess on one coded female coupling part will normally receive the projection on a mating male coupling part, and will not receive the projection on a coupling part for different mating pairs. Likewise, a given male coupling part is capable of having its projection closely received in a recess only in a coded mating female coupling part, and such projection will not be received in different mating coupling parts. These arrangements are shown by way of example with respect to FIGS. 5 and 6. In the arrangement of FIG. 5, a male coupling part 40a has a cylindrical projection 50a of slightly larger diameter than the projection 50 in FIG. 1. Therefore, an attempt to interfit male and female members is prevented by engagement between the outer terminal end 56a of the projection 50a and the outer terminal end 124 of the outer sleeve 104. Even though the spring 46 would be fully compressed, the stem 26 will not extend far enough into the bore 80 to open the fluid control means 72. Because the outer sleeve 104 does not move inwardly at all and is separate from the inner sleeve 102, the ability of the coded coupling parts to inhibit the opening of the valve 72 is enhanced as shown in FIG. 5. Instead of the difference between the coupling parts in FIG. 5 being due to a larger diameter projection 50a on a male sleeve 40a, it will be recognized that this could be due to smaller sizes of inner and outer female sleeves 102 and 104 so that the recess 128 would be of smaller diameter.

Figure 6:
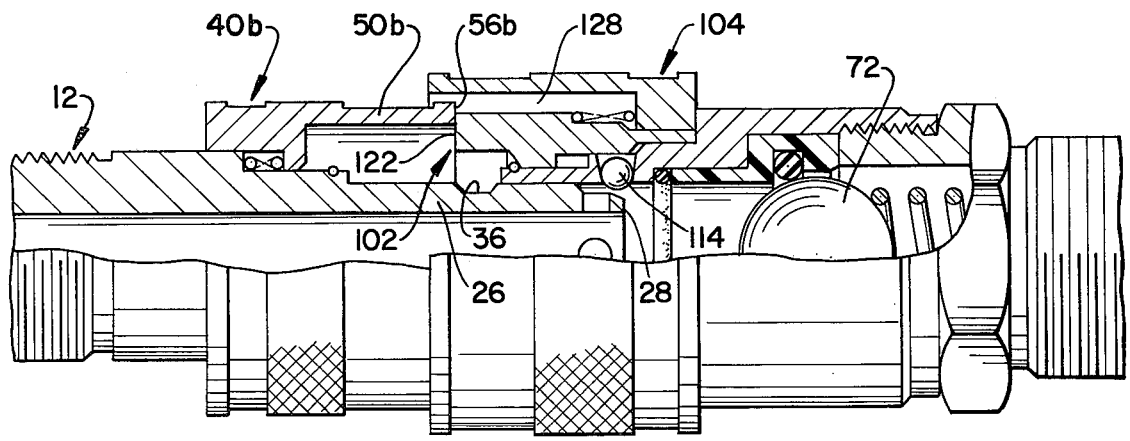
FIG. 6 is a cross-sectional elevational view showing another arrangement of non-mating coupling parts.

FIG. 6 shows an arrangement wherein a smaller diameter projection 50b on a male sleeve 40b has its outer terminal end 56b striking against the outer terminal end 122 of the inner sleeve 102. This engagement between the terminal ends of the projection 50b and the inner sleeve 102 will cause the inner sleeve 102 to move inwardly to its locking position wherein the balls 114 are in their inward position before the stem end 28a has moved therepast so that the stem 26 is not capable of moving past the balls 114 to open the fluid control means 72. Naturally, it is also possible to have a stem 26 move up to the balls 114 but not as far as the groove 36 so that the members cannot be coupled and the fluid control means 72 will not be opened.

In the arrangement of FIG. 6, it will be recognized that the incompatibility can also be due to having the inner and outer sleeves 102 and 104 of larger diameter so that the recess 128 is of larger diameter. FIGS. 5 and 6 are representations of one coded coupling part being ineffective to couple with a different coded part when the two coupling parts have projections and recesses which do not fit closely together. When the coupling parts are compatible, the female and the male members are interfitted over a predetermined axial length as shown in FIG. 3 to open the valve 72. In the arrangement of FIGS. 5 and 6, the non-interchangeability or incompatility between the different sizes of coded coupling parts prevents both interfitting of the male and female members over the predetermined axial length necessary to open the fluid control means 72, and also prevents positive releasable coupling of the members because the stem groove 36 cannot be inserted as far as the balls 114.

Figure 4:
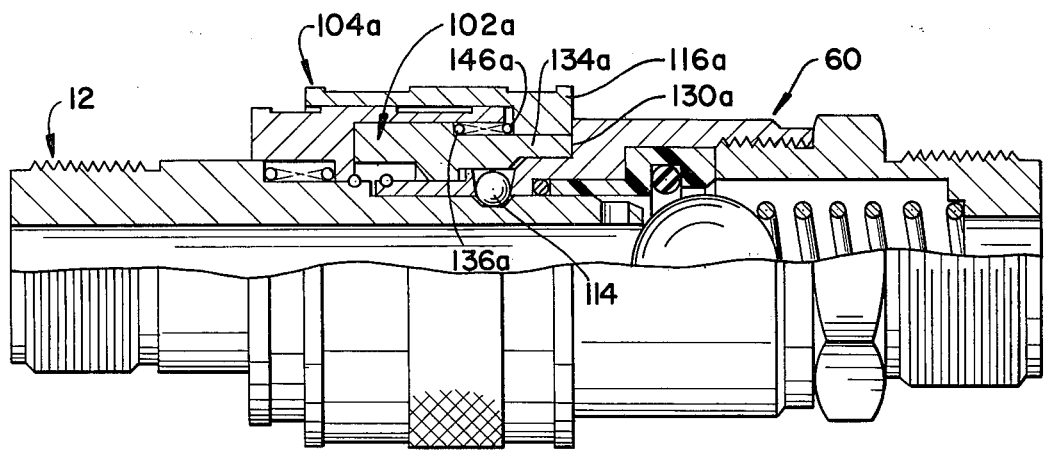
FIG. 4 is a partial cross-sectional elevational view of coupled members having slightly modified coupling parts.

FIG. 4 shows a slightly modified arrangement wherein the inner sleeve 102a lacks the small external cylindrical portion 138 of FIG. 1 adjacent the inner terminal end 130 thereof. Instead, the intermediate external cylindrical portion 134 of FIG. 1 is identified as 134a in FIG. 4 and extends from the shoulder 136a to the terminal end 130a. The base portion 116a of the outer sleeve 104a has a larger bore therein and is axially slidably supported on the external cylindrical surface 134a. This arrangement eliminates the cooperating shoulders 140 and 142 on the inner sleeve 102 and the base portion 116 of FIG. 1 so that pulling on the outer sleeve 104a can move the inner sleeve 102a to the left in FIG. 4 for allowing outward movement of the balls 114 to their outer released positions by fully compressing the coil spring 146a until it bottoms out. In other respects, the embodiment of FIG. 4 operates in the same manner as the embodiments of FIGS. 1–3.

Figure 7:
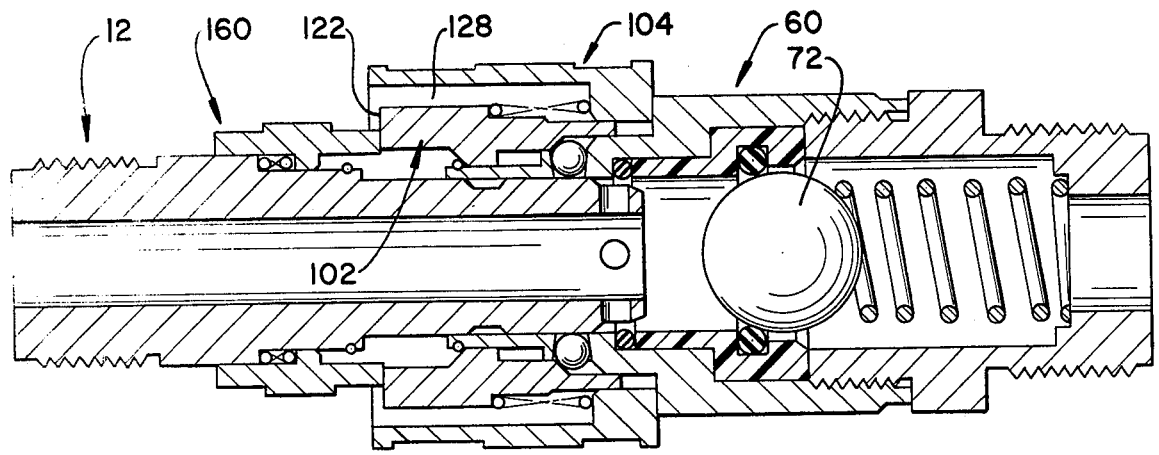
FIG. 7 is a partial cross-sectional elevational view showing a coded female coupling part constructed in accordance with the present invention in an incompatible relationship with a standard male coupling part; and, FIG. 8 is a partial cross-sectional elevational view showing how a standard female coupling part is incompatible with a coded male coupling part constructed in accordance with the present invention.

FIG. 7 shows what occurs when an attempt is made to interfit a male member carrying a standard noncoded male coupling part or sleeve 160 with a coded female coupling part constructed in accordance with the present invention. As shown, the standard noncoded male sleeve 160 lacking any projection receivable in the recess 128 simply abuts the terminal end 122 of the inner sleeve 102 and the male member cannot be interfitted with the female member for the necessary predetermined axial length to open the normally closed fluid control means 72. Thus, coupling is prevented in substantially the same manner as described with reference to FIG. 6.

Figure 8:
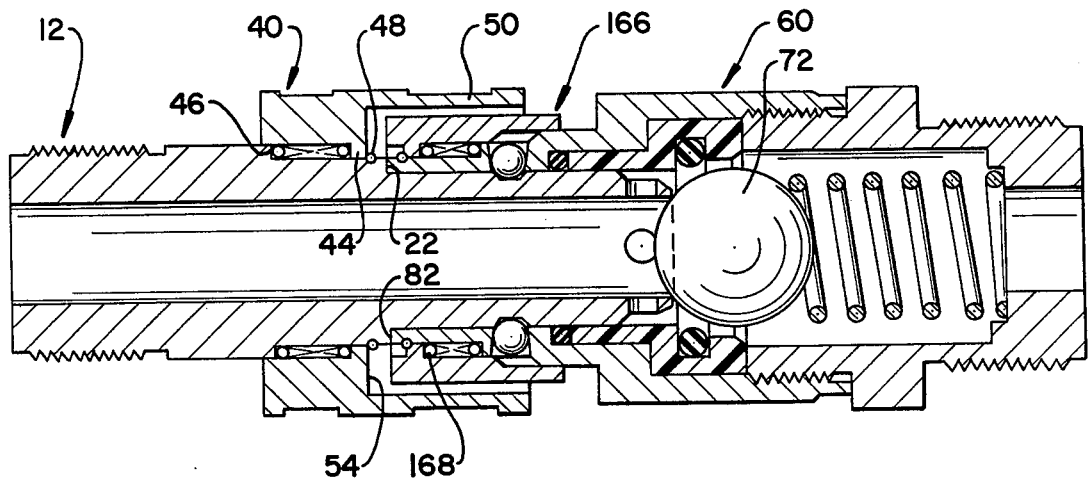

FIG. 8 shows what occurs when an attempt is made to couple a coded male coupling part with a standard female coupling part. As shown, the standard female coupling part or sleeve 166 simply fits within the cylindrical projection 50 on the male coupling part 40. When the male member 12 has been fully extended within the female member 60 so that the fluid control means 72 is opened, shoulder 22 will be abutting the terminal open end 82 of the female member 60. In this position of the parts, the spring 46 biasing the male coupling part 40 to the right is fully extended and the flange 44 is bearing against the stop ring 48. However, the terminal end of the standard female sleeve 166 is not abutting the shoulder 54 on the male coupling part 40 so that the spring 168 holding the standard female sleeve 166 in its unlocked position also remains fully extended and it is not possible to move the standard non-coded female sleeve 166 axially inward to its locking position.

With the system shown and described, it will be recognized that a normal coded system of couplings would include many different mating pairs of coded coupling parts arranged so that each mating pair would mate only with one another and not with any different mating pairs due to the fact that the projections and recesses on the different mating pairs are not interchangeable with other coupling parts. In addition, the coded coupling parts of every mating pair are ineffective to cooperate with standard non-coded male or female coupling parts lacking the projection or recess to closely cooperate with the recess or projection on the coded coupling parts. In the coded system of couplings for interfitting male and female members at least one of which includes normally closed fluid control means moved to an opened position when the members are interfitted over a predetermined axial length, different mating pairs of coded male and female coupling parts are carried by the male and female members for releasably coupling the members when they are interfitted over their predetermined axial length. Coded coupling parts have projections and recesses dimensioned for closely fitting together. Each coupling part of a mating pair is ineffective to positively releasably couple male and female members interfitted over the predetermined axial length when one of the members carries a different coded part or carries a non-coded part lacking a projection or recess.

The coupling parts defined essentially by the male sleeve 40 and the female sleeves 102, 104, can be considered cooperating releasable coupling means carried by the male and female members 12 and 60 for releasably coupling such members. The cooperating projection and recess means defined by the projection 50 and the recess 128 are dimensioned for closely fitting together when the members 12 and 60 are coupled. The inner and outer sleeves 102 and 104 are biased away from one another against the stops 148 and 94 by the yieldable biasing means in the form of spring 146. The spring 46 biasing the male sleeve 40 may be considered to bias the male sleeve 40 outwardly with a first force which is greater than a second force with which the spring 146 biases the inner sleeve 102 outwardly to its unlocking position. Therefore, the first force of the coil spring 46 overcomes the second force of the coil spring 146 for moving the inner sleeve 102 inwardly to its locking position.

Obviously, the disclosed embodiments of the invention are deemed to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A quick connect coupling member having inner and outer sleeves including outer terminal ends located adjacent one another, said sleeves being radially spaced from one another at said outer terminal ends and over at least a portion of their length inwardly from said outer terminal ends to define an axially extending recess opening outwardly between said outer terminal ends, locking detents carried by said coupling member for movement relative thereto between coupling and releasing positions, said inner sleeve cooperating with said locking detents and being axially movable relative to said coupling member and to said outer sleeve between locking and unlocking positions for respectively locking said detents in said coupling position and providing movement of said detents to said releasing position, and yieldable biasing means for normally biasing said inner sleeve to one of said positions.

2. The coupling member of claim 1 wherein said biasing means normally biases said inner sleeve to said unlocking position.

3. The coupling member of claim 1 wherein said outer sleeve is axially movable relative to said coupling member.

4. The coupling member of claim 1 wherein said recess extends over a major portion of the length of said sleeves.

5. A coded quick connect coupling including interfitting male abnd female members carrying coded male and female coupling parts, said coded male coupling part comprising an axially movable male sleeve including an elongated axial projection and a shoulder inwardly of said projection, first yieldable biasing means biasing said male sleeve outwardly with a first force, said female coupling part comprising inner and outer sleeves having outer ends radially spaced apart to define an entrance opening to an elongated recess between said inner and outer sleeves dimensioned and positioned to closely receive said projection when said members are interfitted, said inner and outer sleeves being axially movable relative to said female member and to one another, second yieldable biasing means biasing said inner and outer sleeves apart with a second force, detents carried by said female member movable radially inwardly to a coupling position and outwardly to a releasing position, said male member having a groove receiving said detents when said members are interfitted, said inner sleeve being normally biased to an unlocking position by said second yieldable biasing means for freeing said detents for movement to said releasing position, said inner sleeve being forced axially inwardly to a locking position holding said detents in said groove by action of said first force through engagement of said shoulder with said outer end of said inner sleeve when said members are interfitted.

6. The coupling of claim 5 wherein said inner sleeve has an inner end portion on which said outer sleeve is slidably supported, said inner end portion of said inner sleeve having a smaller diameter than the outer end portion thereof to define a spring cavity inwardly of said recess, and said second biasing means comprising a coil spring positioned in said spring cavity and having spring ends bearing against said inner and outer sleeves.

7. The coupling of claim 5 wherein said inner sleeve has a stepped outer surface including a largest end portion extending axially inwardly from said outer end thereof, a smaller intermediate portion extending inwardly from said largest end portion, and a smallest end portion extending inwardly from said intermediate portion, said outer sleeve having an inner support portion axially slidably supported on said smallest end portion, said second yieldable biasing means comprising a coil spring surrounding said intermediate portion and having spring ends bearing against said inner support portion and the intersection between said largest and intermediate portions, said support portion normally being spaced inwardly from the intersection of said smallest and intermediate portions and being movable outwardly to engage same before said spring is fully compressed.

8. In a system of couplings for interfitting male and female members at least one of which includes normally closed fluid control means which is opened when said members are interfitted over a predetermined axial length, cooperating releasable coupling means on said members for releasably coupling said members, said coupling means including a plurality of different mating pairs of coded male and female coupling parts respectively having closely interfitting projections and recesses so that the projection and recess on a mating pair of male and female coupling parts will not interfit with a recess or projection respectively on other non-mating coded coupling parts, said coded male and female coupling parts preventing interfitting of male and female members carrying same over said predetermined axial length to open said fluid control means unless the coded coupling parts thereon are a mating pair, and a plurality of mating pairs of standard non-coded male and female coupling parts all cooperable with one another and lacking any interfitting projections and recesses, the improvement comprising; each said coded male coupling part comprising a cylindrical sleeve defining said projection and each said coded female coupling part comprising radially spaced inner and outer sleeves between which said recess is defined, and said coded male and female coupling parts respectively being incapable of interacting with standard non-coded female and male coupling parts to positively releasably couple male and female members interfitted over said predetermined axial length.

9. The system of couplings of claim 8 wherein said inner sleeve is axially movable relative to said outer sleeve between locking and unlocking positions, first yieldable biasing means normally biasing said inner sleeve outwardly to said unlocking position with a first force, said male sleeve being biased axially outwardly with a second force greater than said first force by second yieldable biasing means, said male sleeve having an inner shoulder engageable with the outer end of said inner sleeve when said male sleeve is received in said recess so that said second force moves said inner sleeve to said locking position against the biasing action of said first force.

10. A quick connect coupling member having inner and outer sleeves including outer terminal ends located adjacent one another, said sleeves being radially spaced from one another at said outer terminal ends and over at least a portion of their length inwardly from said outer terminal ends to define an axially extending recess opening outwardly between said outer terminal ends, said inner and outer sleeves being axially movable relative to said coupling member, said inner sleeve being axially movable relative to said outer sleeve between locking and unlocking positions, and yieldable biasing means positioned between said sleeves for normally biasing said sleeves away from one another and normally biasing said inner sleeve to one of said positions.

11. The coupling member of claim 10 wherein said sleeves have inner end portions and said outer sleeve is guided for axial movement on said inner end portion of said inner sleeve.

12. A quick connect coupling member having inner and outer sleeves including outer terminal ends located adjacent one another, said sleeves being radially spaced from one another at said outer terminal ends and over at least a portion of their length inwardly from said outer terminal ends to define an axially extending recess opening outwardly between said outer terminal ends, said inner and outer sleeves being axially movable relative to said coupling member, said inner sleeve being axially movable relative to said outer sleeve between locking and unlocking positions, said inner sleeve having an inner end portion on which said outer sleeve is guided, and yieldable biasing means positioned for normally biasing said sleeves apart and normally biasing said inner sleeve to one of said positions.

13. A quick connect coupling member having inner and outer sleeves including outer terminal ends located adjacent one another, said sleeves being radially spaced from one another at said outer terminal ends and over at least a portion of their length inwardly from said outer terminal ends to define an axially extending recess opening outwardly between said outer terminal ends, said inner and outer sleeves being axially movable relative to said coupling member, said inner sleeve being axially movable relative to said outer sleeve between locking and unlocking positions, said sleeves having inner end portions and said inner end portion of said outer sleeve being slidably supported on said inner end portion of said inner sleeve, said inner sleeve having an inwardly extending step providing a shoulder, and yieldable biasing means positioned between said shoulder and said inner end portion of said outer sleeve for normally biasing said sleeves apart and normally biasing said inner sleeve to one of said positions.

14. In a quick connect coupling including interfitting male and female members having cooperating releasable coupling means for releasably coupling said members, said coupling means including an axial projection on one said member and an axial recess on the other of said members dimensioned for closely receiving said projection, said recess being defined between radially spaced inner and outer sleeve parts having outer terminal ends, the improvement comprising; said inner sleeve part being separate from said outer sleeve part and being axially movable relative thereto, said terminal end on said outer sleeve part being axially spaced outwardly of said terminal end on said inner sleeve part a substantial distance at least when said members are coupled with said projection received in said recess, and yieldable biasing means normally biasing said inner sleeve part axially outwardly away from said outer sleeve part.

15. The coupling of claim 14 wherein said outer sleeve part is axially movable relative to said other member on which said sleeves are mounted, said other member having axially spaced stops, and said sleeve parts being biased away from one another against said stops by said yieldable biasing means.

16. A quick connect coupling including interfitting male and female members having cooperating releasable coupling means for releasably coupling said members, said coupling means including cooperating projection and recess means dimensioned and positioned for closely fitting together when said members are coupled in interfitting relationship by said coupling means, said coupling means on said female member including inner and outer sleeves axially movable relative to one another and directly between which said recess means is defined with no other parts of said female member or said coupling means interposed therebetween, said coupling means on said male member including a male sleeve having a cylindrical extension defining said projection means, said inner and outer sleeves having radially spaced outer terminal ends between which an entrance opening to said recess means is defined, and said outer terminal end of said inner sleeve being spaced a substantial distance axially inward of said outer terminal end of said outer sleeve at least when said members are coupled with said extension received in said recess means.

17. A quick connect coupling including interfitting male and female members having cooperating releasable coupling means for releasably coupling said members, said coupling means including cooperating projection and recess means dimensioned and positioned for closely fitting together when said members are coupled in interfitting relationship by said coupling means, said coupling means on said female member including inner and outer sleeves axially movable relative to one another and directly between which said recess means is defined with no other parts of said female member or said coupling means interposed therebetween, said female member carrying generally radially movable detents movable between radially inward and outward positions, said male member having a circumferential groove for receiving said detents, said inner sleeve being axially movable between a locking position holding said detents in said inward position and an unlocking position allowing movement of said detents to said outward position, yieldable biasing means normally biasing said inner sleeve to said unlocking position, and said inner sleeve being held in said locking position when said male and female members are coupled by said cooperating releasable coupling means.

18. The coupling of claim 17 wherein said outer sleeve is movable axially of said female member for moving said inner sleeve to said unlocking position to uncouple said male and female members.

19. In a system of couplings for interfitting male and female members at least one of which includes normally closed fluid control means which is opened when said members are interfitted over a predetermined axial length, cooperating releasable coupling means on said members for releasably coupling said members, said coupling means including a plurality of different mating pairs of coded male and female coupling parts respectively having closely interfitting projections and recesses so that the projection and recess on a mating pair of male and female coupling parts will not interfit with a recess or projection respectively on other non-mating coded coupling parts, a plurality of mating pairs of standard non-coded male and female coupling parts all cooperable with one another and lacking any interfitting projections and recesses, at least one said coupling part in each said mating pair being movable between a released position in which said male and female members are freely coupleable and separable and a locked position in which said male and female members are positively coupled in interfitted relationship over said predetermined length against separation, said coupling parts on each said mating pair cooperating with one another to provide movement of the movable coupling part to said locking position when the male and female members carrying such coupling parts are interfitted over said predetermined length, and said coded male and female coupling parts respectively being incapable of cooperating with standard non-coded female and male coupling parts to provide movement of the movable coupling part to its locked position, whereby said coded coupling parts are cooperable only in mating pairs to positively couple male and female members interfitted over said predetermined length and are incapable of cooperating in non-mating pairs or with standard non-coded coupling parts to positively couple the male and female members interfitted over said predetermined length.

* * * * *